United States Patent [19]

Combier et al.

[11] 4,335,113
[45] Jun. 15, 1982

[54] TRITERPENIC SAPONIN HAVING PHARMACOLOGICAL POTENCY

[75] Inventors: Henri Combier, Rilleux le Pape; Gisele Prat, Talence; Henri Pontagnier, Pessac, all of France

[73] Assignee: Laboratoires Sarget, Merignac, France

[21] Appl. No.: 148,932

[22] Filed: May 12, 1980

[30] Foreign Application Priority Data

May 11, 1979 [FR] France ................... 79 11964

[51] Int. Cl.³ ............... A61K 31/70; C07H 15/20
[52] U.S. Cl. ................... 424/180; 536/5; 536/18.1
[58] Field of Search ................ 536/4; 424/180

[56] References Cited

U.S. PATENT DOCUMENTS

| 3,163,636 | 12/1964 | Wagner et al. | 536/4 |
| 3,238,190 | 3/1966 | Erbring et al. | 536/4 |
| 3,713,980 | 1/1973 | Balsam et al. | 536/4 |
| 3,723,410 | 3/1973 | Persinos | 536/4 |
| 4,148,928 | 4/1979 | Sodini et al. | 536/4 |
| 4,171,430 | 10/1979 | Matsushita et al. | 536/4 |

OTHER PUBLICATIONS

Strigina et al., "Chem. Abst.", vol. 82, 1975, 125,562j).

Primary Examiner—Johnnie R. Brown
Attorney, Agent, or Firm—Oblon, Fisher, Spivak, McClelland & Maier

[57] ABSTRACT

The present invention concerns a new triterpenic saponin derived from caulophyllogenin, the process for extracting it from varieties of Chrysanthellum, and its therapeutic use.

This saponin is characterized as being the ester of O-$\beta$-D-glucosyl-3$\beta$-caulophyllogenin and an oligosaccharide comprising two units of L-rhamnose and two units of D-xylose. It is extracted from vegetable matter and purified using pressurized liquid preparative chromatographic techniques.

This saponin is useful in human and veterinary therapeutics in phlebology, rheumatology, and traumatology.

7 Claims, No Drawings

TRITERPENIC SAPONIN HAVING PHARMACOLOGICAL POTENCY

BACKGROUND OF THE INVENTION

1. Field of the Invention

The present invention concerns a new triterpenic saponin, the process by which it is obtained, and its use as a medicine useful in human and veterinary therapeutics.

2. Description of the Prior Art

The plants of the genus Chrysanthellum (Compositae family) are tropical and equatorial savannah plants found in the hot regions of both hemispheres. As a result of the climate of these regions, harvesting may occur all year long upon successive flowerings of the plants. These plants contain several products useful in therapeutics. French patents 979 M and 70.25949 describe respectively the aqeuous and hydroalcoholic extracts of Chrysantellum procumbens Rich and Chrysanthellum americanum Vatke. French Pat. No. 74.22371 describes the powdered polyphenolic extracts obtained from plants of the Chrysanthellum genus. French Pat. No. 77.01488 describes a Chrysanthellum extract rich in triterpenic component and containing, as its principal ingredient, a new saponin derived from echinocystic acid.

SUMMARY OF THE INVENTION

We have now demonstrated, in plants of genus Chrysanthellum, the existence of a new saponin derived from caulophyllogenin and having a pharmacological potency which enables its use in human and veterinary therapeutics.

DETAILED DESCRIPTION OF THE PREFERRED EMBODIMENTS

Caulophyllogenin, or trihydroxy-$3\beta$, $16\alpha$, 23 oleanene-12 oic-28 acid, is a triterpenic sapogenin which is relatively rare in the vegetable kingdom, since its presence has has to date been pointed out only in Caulphyllum robustum, from which it is extracted in the form of arabinoside, the B cauloside (works of L. I. Strigina et coll., Phytochemistry 13, 479-80 (1974), and Khim. Prir. Soedin. 6, 733-8 (1974), Chem. Abstr. 82, 125562 j). We have discovered the presence of this sapongenin in species of genus Chrysanthellum in the form of a new glycoside (the ester of O-$\beta$-D-glucosyl-$3\beta$-caulophyllogenin and an oligosaccharide S) having the structure:

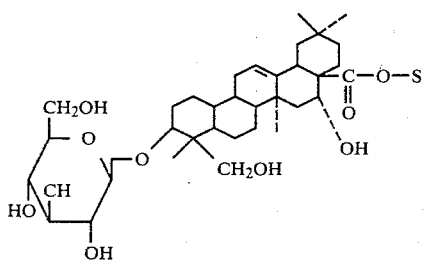

with S=oligosaccharide comprising 2 units of L-rhamnose and 2 units of D-xylose.

The glycoside which is the object of the present patent is obtained by a process according to which the vegetable matter is extracted with an organic solvent such as heated methanol. The organic phase is concentrated, water is added and fats removed. The solvent is eliminated. Part of the saponin precipitates, with the other triterpenic constituents of the vegetable matter; the greater part of the saponin remains in aqueous solution from which it is separated by extraction using ethyl acetate followed by a mixture of n-butanol and benzene. The butylic phases are recovered with methanol, following concentration, and treated with activated charcoal. After filtering and drying, a second, solid fraction containing the saponin is obtained. This is separated and purified using known chromatographic techniques.

In the following example, we shall describe more precisely the techniques for extraction and purification of this new saponin.

EXAMPLE

Two kg of Chrysanthellum procumbens (dried whole plant) are extracted three times with 10 l of heated methanol. The methanolic solutions are concentrated to a volume of 1 l and then supplemented with 1 l of water. Fats are removed from the mixture with three times 1 liter of chloroform. The methanol is eliminated by rotary evaporation and the precipitate washed and filtered. This first extract, weighing 5 g, contains 20–50% saponin derived from the caulophyllogenin. The residual aqueous phase is extracted with ethyl acetate followed by a mixture of n-butanol/benzene (4/1, V/V). After concentration, the butylic phases are recovered with 1 liter of methanol and treated with 200 g of activated charcoal. After filtration and drying, a second extract of 20 g, containing the same percentage of saponin as the first, is obtained. The two extracts are combined and the saponin is purified successively by chromatography on an open column of silica in a gradient of $CHCl_3/CH_3OH/H_2O$ (65/25/10 to 50/40/10, V/V/V), by pressurized liquid preparative chromatography (Waters Associates Prep. 500 apparatus) in the solvent ethyl acetate/methanol/water (100/25/10), by pressurized liquid preparative chromatography on a $C_{18}$ inverted phase support column (Waters Associates apparatus) in the solvent methanol/water (70/30).

Thus separated and purified, the saponin has the following chromatographic characteristics:

thin silica layer chromatography in solvent of ethyl acetate/methanol/water (100/25/10, V/V/V) following development with p-anisaldehyde (reagent $CH_3COOH$/p-anisaldehyde/$H_2SO_4$, 40/1/1, V/V/V, activation 10 mins. at 100° C.) $R_f \sim 0.28$.

high performance liquid chromatography in inverted phases ($C_{18}$ Bondapak $\mu$ column 30 cm long, 4 mm in internal diameter, with granulometry of $10\mu$; solvent methanol/water/$Ch_3COOH$, 70/29/1, V/V/V, flow rate 1 ml/min., detection using Waters Associates refractometer) $k' = 1.35$.

The structure of the saponin thus obtained was determined in the following manner:

Aglycon and sugars are obtained by acid hydrolysis using a mixture of $H_2SO_4$/dioxan/water for six hours. The precipitate which results from this hydrolysis consists of sapogenin having the following physical-chemical characteristics:

Sapogenin, empirical formula $C_{30}H_{48}O_5$ thin silica layer chromatography in solvent of chloroform/methanol (95/5, V/V), developed with p-anisaldehyde: $R_f = 0.30$.

F=280° C.

Mass spectrum, molecular ion M+·=488, principal fragments m/e 264 (33%), 246 (100%), and 201 (65%) characteristic of reverse Diels-Alder fragmentation of oleanene-12s having an OH and a COOH on the D and/or E nucleus.

NMR of $^{13}C$ (internal reference TMS). Presence of six quaternary C appearing in form of off-resonance singlet (C4 39.9 ppm, C8 42 ppm, C14 42.7 ppm, C17 48.8 ppm, C20 31 ppm).

The chemical displacements of ethylene carbons C12 (122.3) and C13 (144.9) are characteristic of the oleanene-12 series. The hydroxylated carbons appear in the 60–80 ppm region (C23 with a primary alcohol: 68.1 ppm giving an off-resonance triplet; C3 with an equatorial OH: 73.5 ppm, doublet; C16 with axial OH: 74.6 ppm, doublet).

SAPOGENIN METHYLATED USING DIAZOMETHANE

Mass spectrum, M+·=502 and principal fragments m/e 278 (11%), 260 (84%) and 201 (100%).

ACETYLATED SAPOGENIN

Proton NMR at 100 MHz in $CDCl_3$, δ expressed in ppm.

Presence of 6 $CH_3$ δ=0.74 (3H, s); 0.84 (3H, s); 0.96 (3H, s); 1.02 (6H, s); 1.26 (3H, s).

Presence of 3 acetyl δ=2.06 (3H, s); 2.10 (3H, s); 2.12 (3H, s).

Presence of an acetylated methylene —$CH_2$—OAc conducing to an AB system δ3.72 (1H, d, J=12 Hz) and 3.90 (1H, d, J=12 Hz).

C3 proton in axial position δ=4.82 (1H, t, J=7 Hz).

C16 proton in equatorial position δ=5.66 (1H, deformed s).

Ethylenic proton of C12 δ=5.46 (1H, deformed s).

Study of the aqueous phase resulting from acid hydrolysis enables, after neutralization, a determination to be made of the nature and composition of the sugars.

Descending paper chromatography in solvent n-butanol/pyridine/water (6/4/3, V/V/V) enables detection, after development with silver nitrate, of the presence of rhamnose, xylose and glucose. Analysis of the sugars in the form of alditol acetates by gaseous phase chromatography (ECNSS-M column at 3% on Gas Chrom Q 80-100 mesh) confirms the nature of the sugars and shows that they exist in the ratio glucose 1:rhamnose 2:xylose 2.

Determination of the specific rotations of each of the sugars gives the configurations D-glucose, D-xylose and L-rhamnose.

Alcaline hydrolysis of the saponin with NaHO 0.1 N enables, after purification by silica column chromatography in solvent of ethyl acetate/methanol/water (25/2/1, V/V/V), isolation of a triterpenic derivative. Acid hydrolysis of the latter frees aglycon (caulophyllogenin) and a sugar-characterized by descending paper chromatography (with solvent n-butanol/pyridine/water, 6/4/3, V/V/V) and gaseous phase chromatography in the form of alditol acetate, as being glucose. The position of glucose on the sapogenin was determined by NMR OF $^{13}C$.

In fact, if the NMR spectra of caulophyllogenin and its glucoside are compared, the results given in the following table are obtained:

| Carbon no. | Chemical displacement δ in ppm | | Difference: δ glucoside − δ sapogenin |
|---|---|---|---|
| | Glucoside of caulophyllogenin | Caulophyllogenin | |
| 3 | 82.1 | 73.5 | 8.6 |
| 16 | 74.6 | 74.6 | 0 |
| 23 | 64.7 | 68.1 | −3.4 |
| 24 | 13.6 | 13 | 0.6 |
| 25 | 16.2 | 16 | 0.2 |

These results accord with the glucosylation of the alcohol in C3. We further show in the spectrum of caulophyllogenin glucoside, evidence of the anomer carbon C1 at 105.6 ppm. This displacement is characteristic of a β-D-glucose bond. The four other sugars of the saponin form an oligosaccharide linked to the sapogenin by the carboxyl group in C28.

We determined the potency of the saponin derived from caulophyllogenin as prepared above in the following tests:

Acute toxicity was determined in the EOPS mouse, CD1 strain, with the product administered interperitoneally in neutralized physiologic solution (pH ~6.8). A 15 mg/kg dose shows no mortality. Doses of 17.5 mg/kg and 20 mg/kg result respectively in 10 and 90% mortality (determined following a 14 day observation period). This saponin is therefore much less toxic than -aescine, of which LD 50 in the same conditions is 3.2 mg/kg.

Analgesic potency was determined in a test using phenyl p-benzoquinone (PBQ). A hydroalcoholic solution with 0.02% PBQ is administered interperitoneally to male EOPS mice of the CD1 strain. After 5 minutes, this solution causes stomach spasms and extension of the back feet of the mice. The saponin is administered interperitoneally in neutralized physiological solution 10 minutes before the PBQ. The analgesic ED 50 is calculated from the regression line expressing the number of contractions as a function of the dose. It is 2.1 mg/kg (1.5–2.34) compared to 2.7 (1.7–7.5) for β-aescine administered under the same conditions.

Effect on capillary resistance was determined by a variant of the method of Charlier R., Hosslet A. and Colot M. (*Arch. inter. Physiol. Biochem.* 71, 1–45 (1963)) on O.F.A. EOPS rats. The saponin is administered interperitoneally in solution in distilled water at pH 7. The potency of the saponin, expressed in units cm Hg/h, is 11.5±10.6 (NS) at mg/kg; 16.5±12 (NS) at 2.5 mg/kg; 29.5±21.8 (S 1%) at 4 mg/kg; 27.7±12.3 (S 1%) at 5 mg/kg; and 59.75±28 (S 1%) at 6 mg/kg. Administered under the same conditions, aescine has a potency of 41.2±17 (S 1%) at 5 mg/kg; 72.2±13 (S 1%) at 7.5 mg/kg and 84.2±19.8 (S 1%) at 10 mg/kg.

Effect on capillary permeability is determined by the method of Charlier R., Hosslet A. and Canivet L (*Arch. inter. Physiol. Biochem.* 71, 51–63 (1963)) in the conventional Wistar rat. Administered interperitoneally, the saponin produces a Non-Significant reduction in capillar permeability at 1 mg/kg, 20% at 2.5 mg/kg (S 1%), 38% at 5 mg/kg, 41% at 7.5 mg/kg, and 45% at 10 mg/kg, the latter three effects being significant at 1%. Under the same conditions, the effect induced by β-aescine is 17% at 1 mg/kg (NS), 56% at 5 mg/kg (S 1%), and 70% at 10 mg/kg (S 1%).

Considering its pharmacological properties, especially its good therapeutic index in comparison with the reference product, β-aescine, the saponin which constitutes the object of the present invention may be used curatively or preventively in phlebology, rheumatology, and traumatology. For example, it might be employed in the course of treating varicose veins, hemorrhoids, oedema, periphlebitus, purpura, arterial hypertension, and hemorrhagic syndromes. It can be administered in association with an appropriate vehicle, e.g., orally in the form of pills, capsules, sugar-coated pills, drops, syrups, and ampoules in doses of from 10–200 mg per day spread over two or three daily ingestions; or locally in the form of ointments, gels, cremes, and powders. It may be joined with other therapeutic substances such as vasodilators, steroid or non-steroid anti-inflammatants, antibiotics, or vitamins.

We indicate non-limitatively some formulae for medications administrable to man:

| Pills: | |
|---|---|
| Saponin according to the present invention | 10 mg |
| Excipient in sufficient quantity for | 1 pill |
| Gel: | |
| Saponin according to the present invention | 3 g |
| Excipient sqf | 100 g |

We claim:

1. A substantially pure saponin which is the ester of O-β-D-glycosyl-3β-caulophyllogenin and an oligosaccharide comprising two units of L-rhamnose and two units of D-xylose having the formula

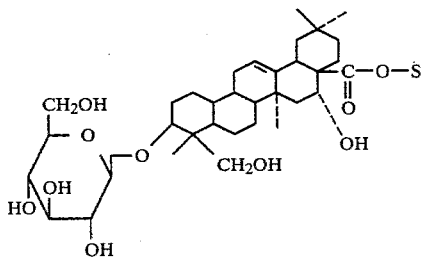

wherein S is the oligosaccharide comprising two units of L-rhamnose and two units of D-xylose.

2. Process for obtaining the saponin according to claim 1, which comprises:
   extracting vegetable matter of the genus Chrysanthellum with an organic solvent;
   concentrating the organic solvent phase of said extraction;
   admixing water with said organic phase;
   removing fats from the admixture of water and organic phase;
   removing the organic solvent from said admixture; and
   recovering the saponin from the precipitate and aqueous phase resulting from the removal of the organic solvent.

3. Process according to claim 2, wherein the saponin is recovered from the aqueous phase by
   extraction of the aqueous phase with ethyl acetate followed by a mixture of n-butanol and benzene, and the butylic phases are recovered with methanol, following concentration, and treated with activated charcoal; thereafter, the methanol-recovered butylic phases are filtered and dried; and the saponin is separated from the resulting precipitate by pressurized liquid preparative chromatography.

4. Process according to claim 2, wherein the organic solvent is methanol.

5. Process according to claim 2, wherein the saponin is recovered from the precipitate by pressurized liquid preparative chromatography.

6. Process for obtaining the saponin according to claim 1, which comprises:
   extracting vegetable matter of the genus Chrysanthellum with an organic solvent;
   concentrating the organic solvent phase of said extraction;
   admixing water with said organic phase;
   removing fats from the admixture of water and organic phase;
   removing the organic solvent from the admixture of water and organic phase;
   recovering a first precipitate after removal of the organic solvent, and washing and drying said first precipitate;
   recovering the aqueous phase after removal of the organic solvent;
   extracting the aqueous phase with ethyl acetate followed by a mixture of n-butanol and benzene, and the butylic phases are recovered with methanol, following concentration, and treated with activated charcoal;
   thereafter the methanol-recovered butylic phases are filtered and dried yielding a second precipitate;
   said first precipitate and said second precipitate are combined and the saponin is separated from the mixture by pressurized liquid preparative chromatography.

7. A pharmacological composition comprising an amount of the saponin according to claim 1 effective to increase capillary resistance while simultaneously reducing capillary permeability and a pharmaceutically acceptable diluent.

* * * * *